(12) United States Patent
Abe et al.

(10) Patent No.: US 9,480,460 B2
(45) Date of Patent: Nov. 1, 2016

(54) ULTRASONIC DIAGNOSTIC APPARATUS AND ULTRASONIC WAVE TRANSMISSION/RECEPTION CONTROL METHOD

(75) Inventors: Yoshihito Abe, Utsunomiya (JP); Shigeru Akiyama, Nasushiobara (JP); Tatsuya Funaki, Otawara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 705 days.

(21) Appl. No.: 13/591,978

(22) Filed: Aug. 22, 2012

(65) Prior Publication Data

US 2012/0312098 A1 Dec. 13, 2012

Related U.S. Application Data

(63) Continuation of application No. PCT/JP2012/064212, filed on May 31, 2012.

(30) Foreign Application Priority Data

Jun. 1, 2011 (JP) ................................ 2011-123590

(51) Int. Cl.
*A61B 8/00* (2006.01)

(52) U.S. Cl.
CPC . *A61B 8/54* (2013.01); *A61B 8/00* (2013.01); *A61B 8/4416* (2013.01)

(58) Field of Classification Search
CPC .............................. A61B 8/54; A61B 8/4416
USPC .................................................. 600/437, 441
See application file for complete search history.

(56) References Cited

U.S. PATENT DOCUMENTS

| | | |
|---|---|---|
| 5,509,413 A | 4/1996 | Akama et al. |
| 2007/0010744 A1 | 1/2007 | Nakamura et al. |
| 2009/0171215 A1 | 7/2009 | Kato et al. |

FOREIGN PATENT DOCUMENTS

| | | |
|---|---|---|
| CN | 1805709 A | 7/2006 |
| JP | 63240843 A | 10/1988 |
| JP | 7-51263 A | 2/1995 |
| JP | 7-67877 A | 3/1995 |

(Continued)

OTHER PUBLICATIONS

The International Search Report (in English) corresponding to International Application No. PCT/JP2012/064212 mailed on Jul. 31, 2012.

(Continued)

*Primary Examiner* — Rajeev Siripurapu
(74) *Attorney, Agent, or Firm* — Kenichiro Yoshida

(57) ABSTRACT

An ultrasonic diagnostic apparatus includes an memory, an determination unit, an instruction unit, a specifying unit, and an redetermination unit. The memory stores upper limit values of parameters for restricting the powers in display modes. The determination unit determines the powers in the modes so as not to exceed upper limit values of the parameters. The instruction unit inputs an instruction to increase/decrease the power of a specific mode. The specifying unit specifies the parameter value in the specific mode. The redetermination unit determines an upper limit value of the parameter in a mode different from the specific mode based on the upper limit value of the parameter in the specific mode and the parameter value specified by the specifying unit.

12 Claims, 9 Drawing Sheets

(56) References Cited

FOREIGN PATENT DOCUMENTS

| | | |
|---|---|---|
| JP | 2009-142473 A | 7/2009 |
| JP | 2009-153674 A | 7/2009 |
| WO | 2011013329 A1 | 2/2011 |

OTHER PUBLICATIONS

Chinese Office Action with its English translation for Chinese Patent Application No. 201280000546.6 mailed on Apr. 3, 2014.
International Search Report dated Jul. 18, 2012 for corresponding International Application No. PCT/JP2012/064212.

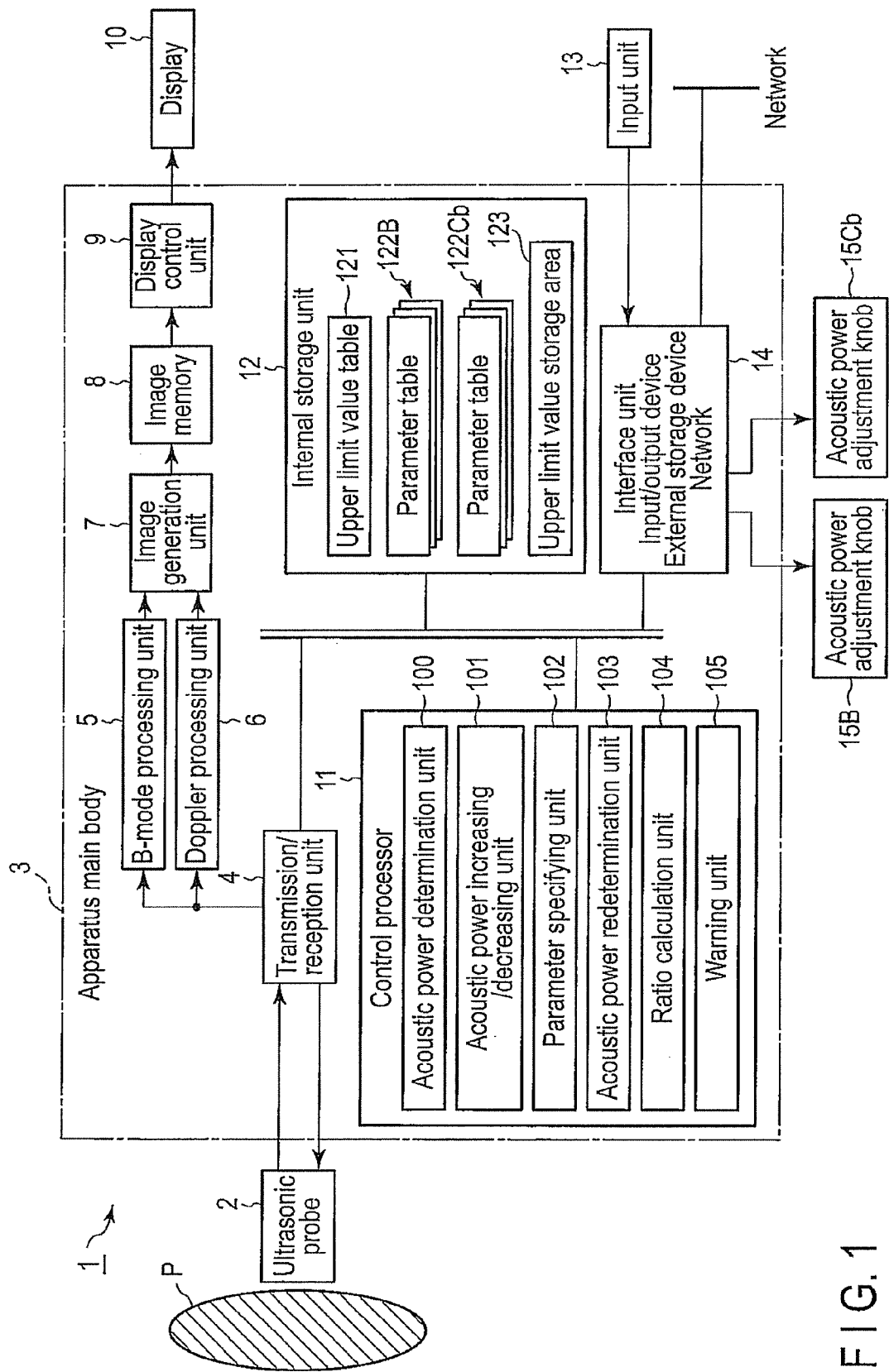
F I G. 1

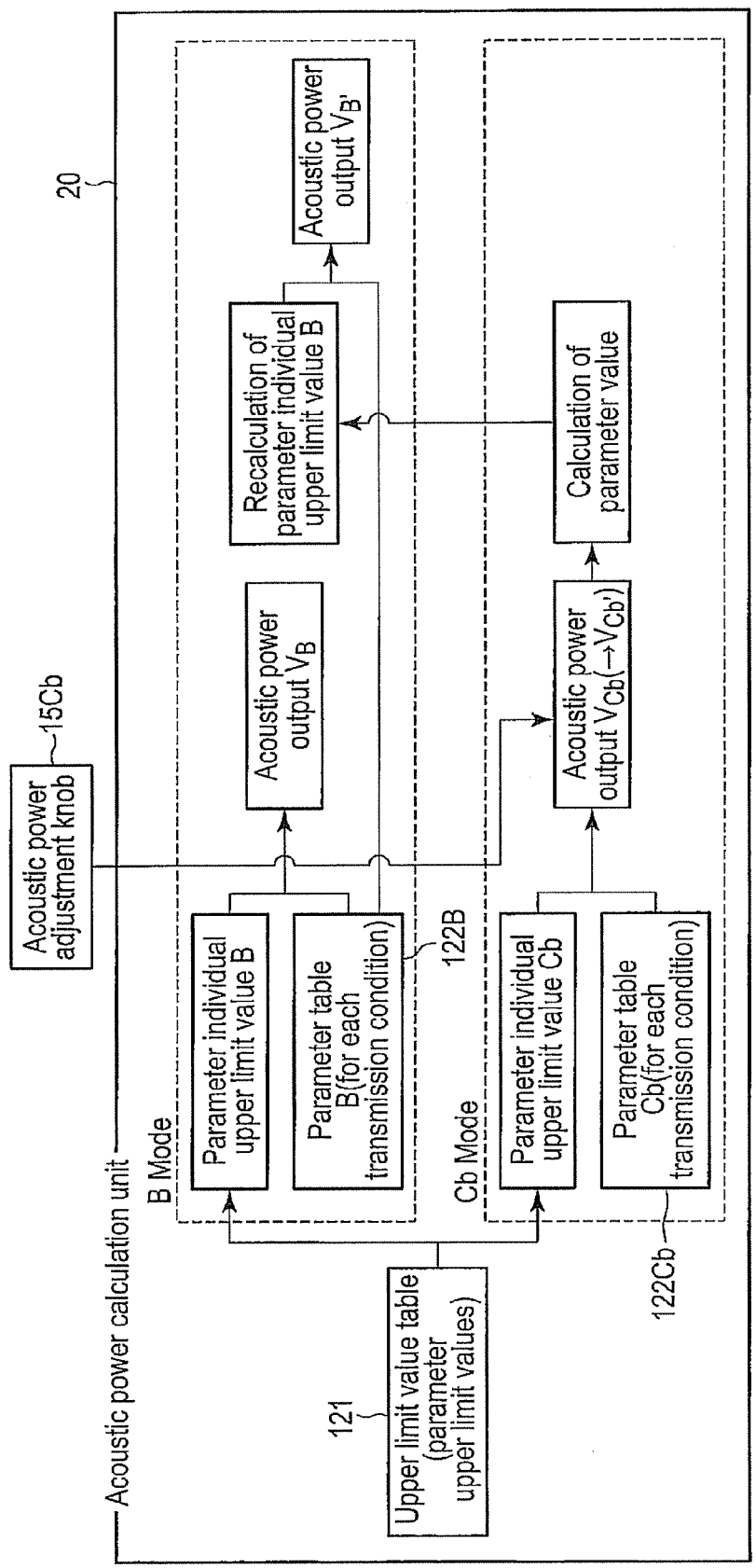
F I G. 6

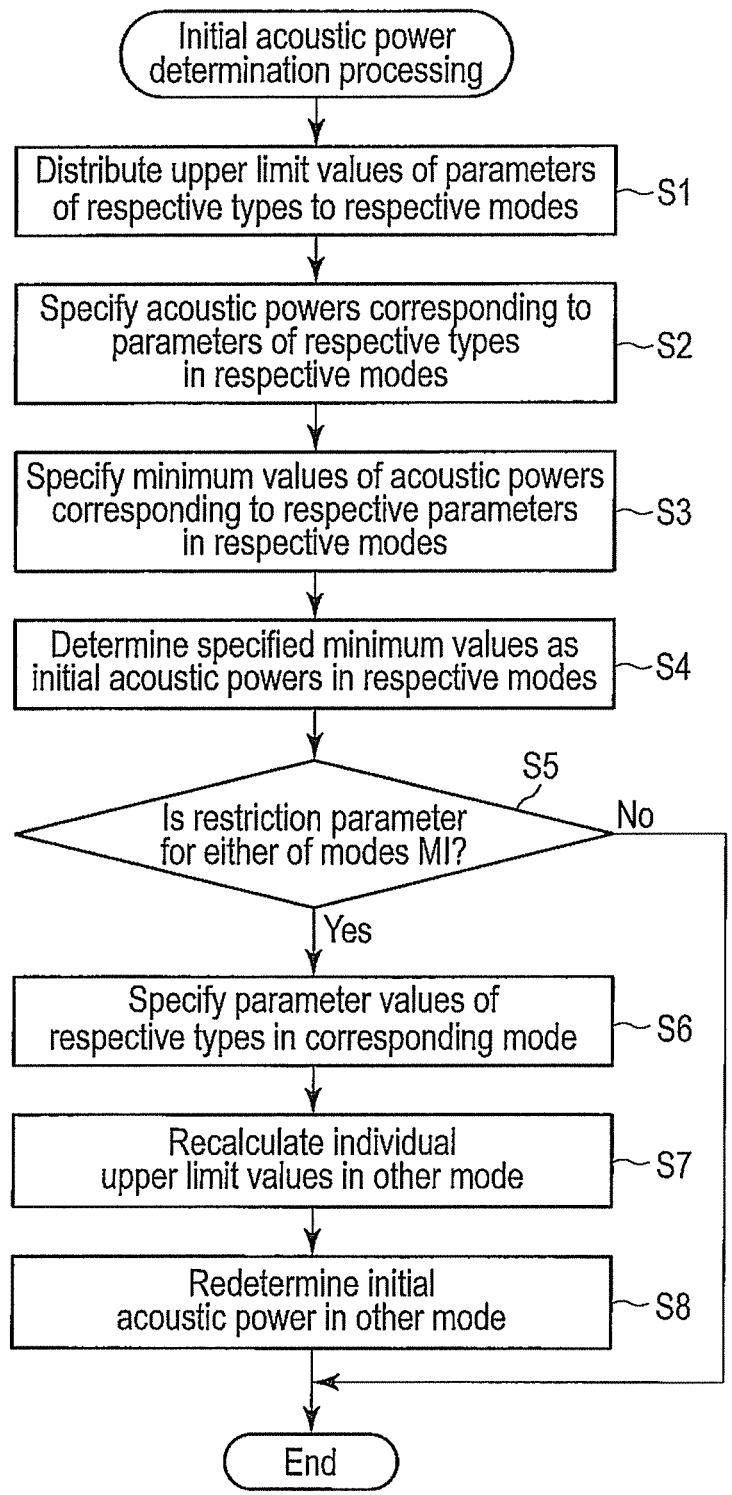
F I G. 11

ULTRASONIC DIAGNOSTIC APPARATUS AND ULTRASONIC WAVE TRANSMISSION/RECEPTION CONTROL METHOD

CROSS REFERENCE TO RELATED APPLICATIONS

This application is a Continuation Application of PCT Application No. PCT/JP2012/064212, filed May 31, 2012 and based upon and claiming the benefit of priority from Japanese Patent Application No. 2011-123590, filed Jun. 1, 2011, the entire contents of all of which are incorporated herein by reference.

FIELD

Embodiments described herein relate generally to an ultrasonic diagnostic apparatus which images the interior of an object and performs diagnosis and an ultrasonic wave transmission/reception control method.

BACKGROUND

An ultrasonic diagnostic apparatus is a diagnostic apparatus which acquires and displays an ultrasonic image of biological information. This apparatus is used as a useful apparatus which is inexpensive, free from radiation, and used for real time, noninvasive observation as compared with other image diagnostic apparatuses such as an X ray diagnostic apparatus and X ray computed tomography apparatus.

When performing ultrasonic diagnosis on a living body by using an ultrasonic diagnostic apparatus, the upper limit of the acoustic power of ultrasonic waves output from an ultrasonic probe is determined in consideration of safety standard. In order to observe this safety standard, this apparatus controls acoustic powers so as not to make the following parameters exceed their upper limits: Ispta (spatial peak temporal average intensity).3 which is the temporal average value of the highest intensities of sounds in an acoustic field, MI (Mechanical Index) which is an index associated with a mechanical action of ultrasonic waves on the living body, TI (Thermal Index) which is an index associated with the thermal action of ultrasonic waves on the living body, and TempRise (probe surface temperature rise).

In a mode constituted by a plurality of display modes, like a color mode, (to be referred to as a combination mode hereinafter), it is necessary to control acoustic powers in the respective display modes so as not to make the sums of values in the respective display modes exceed the upper limit values with respect to Ispta.3, Ti, and TempRise and not to make the maximum value of the values of MI in the respective display modes exceed the upper limit value.

Conventionally, it is possible to decrease the acoustic powers in the respective display modes of the above combination mode by operating the adjustment knobs provided on the ultrasonic diagnostic apparatus. However, the apparatus is not provided with any means for increasing the acoustic powers in the respective display modes from the viewpoint of preventing each parameter described above from exceeding the upper limit value. In addition, the default acoustic power output ratios in the respective display modes have been derived from the fixed ratios set in advance in a table or the like in the ultrasonic diagnostic apparatus. For this reason, the user cannot increase the sensitivity of a specific display mode by freely changing the acoustic power output ratios in the respective display modes.

BRIEF DESCRIPTION OF THE DRAWINGS

FIG. 1 is a block diagram showing the arrangement of an ultrasonic diagnostic apparatus according to the first embodiment.

FIG. 6 is a functional block diagram of the acoustic power calculation unit in the first embodiment.

FIG. 11 is a flowchart for initial acoustic power determination processing in the second embodiment.

DETAILED DESCRIPTION

Figure 2:
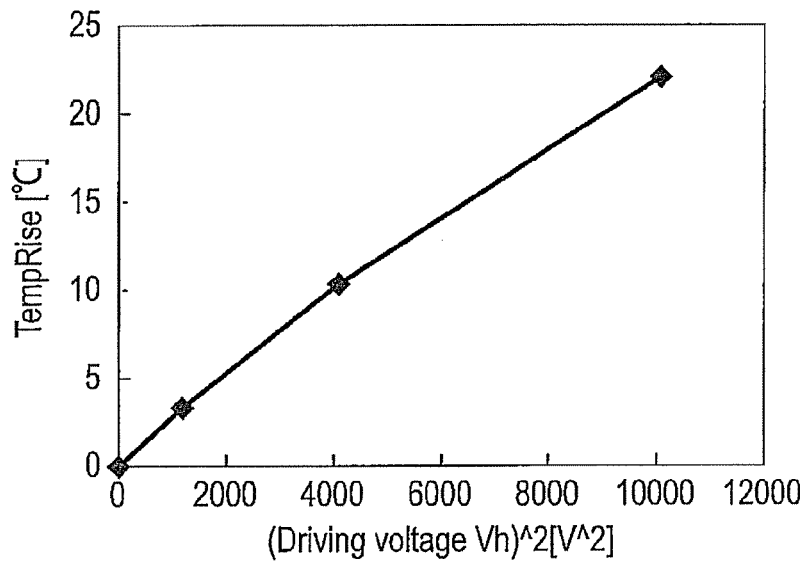
FIG. 2 is a graph showing an example of a parameter table in the first embodiment.

In general, according to one embodiment, an ultrasonic diagnostic apparatus which drives an ultrasonic probe with acoustic powers corresponding to a plurality of display modes for a predetermined time width at a time so as to transmit and receive ultrasonic waves, includes an upper limit storage unit, an acoustic power determination unit, an increase/decrease instruction unit, a parameter specifying unit, and an acoustic power redetermination unit.

The upper limit storage unit stores upper limit values of parameters for restricting the acoustic powers in the respective display modes. The acoustic power determination unit determines the acoustic powers in the respective display modes so as not to exceed upper limit values of the parameters stored in the upper limit storage unit. The increase/decrease instruction unit inputs an instruction to increase/decrease an acoustic power, of the acoustic powers determined by the acoustic power determination unit, which is associated with a specific display mode. The parameter specifying unit specifies the parameter value in the specific display mode in accordance with an input from the increase/decrease instruction unit. The acoustic power redetermination unit determines an upper limit value of the parameter in a display mode different from the specific display mode based on the upper limit value of the parameter in the specific display mode stored in the upper limit storage unit and the parameter value specified by the parameter specifying unit.

Several embodiments will be described below with reference to the accompanying drawings.

First Embodiment

The first embodiment will be described first.
[Apparatus Configuration]

FIG. 1 is a block diagram showing the arrangement of an ultrasonic diagnostic apparatus 1 in this embodiment.

As shown in FIG. 1, the ultrasonic diagnostic apparatus 1 includes an ultrasonic probe 2, an apparatus main body 3, a transmission/reception unit 4, a B-mode processing unit 5, a Doppler processing unit 6, an image generation unit 7, an image memory 8, a display control unit 9, a display 10, a control processor 11, an internal storage unit 12, an input unit 13, an interface unit 14, and acoustic power adjustment knobs 15B and 15Cb.

The ultrasonic probe 2 includes a plurality of piezoelectric transducers which generate ultrasonic waves based on driving signals from the transmission/reception unit 4 and convert reflected waves from an object into electrical signals, a matching layer provided for the piezoelectric transducers, and a backing member which prevents ultrasonic waves from propagating backward from the piezoelectric transducers. When the ultrasonic probe 2 transmits an ultrasonic wave to an object P, the transmitted ultrasonic wave is sequentially reflected by a discontinuity surface of acoustic impedance of internal body tissue, and is received as an echo signal by the ultrasonic probe 2. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The transmission/reception unit 4 includes, as a transmission system, a pulse generator, a delay circuit, and a pulser. The pulser repetitively generates rate pulses for the formation of transmission ultrasonic waves at a predetermined rate frequency fr [Hz] (period: 1/fr sec). The delay circuit gives each rate pulse a delay time necessary to focus an ultrasonic wave into a beam and determine transmission directivity for each channel. The pulse generator applies a driving pulse to the ultrasonic probe 2 at the timing based on this rate pulse after this delay time is given.

The transmission/reception unit 4 also includes, as a reception system, a preamplifier, an A/D converter, a reception delay unit, and an adder. The preamplifier amplifies an echo signal captured via the probe 2 for each channel. The reception delay unit gives the amplified echo signals delay times necessary to determine reception directivities. The adder then adds the echo signals given the delay times. With this addition, the reflection component of the echo signal from the direction corresponding to the reception directivity is enhanced, and a synthetic beam for ultrasonic transmission/reception is formed in accordance with the reception directivity and transmission directivity.

The B-mode processing unit 5 includes a detector and a logarithmic compressor. The detector receives an echo signal from the transmission/reception unit 4, and performs envelope detection processing. The logarithmic compressor performs logarithmic amplification for the echo signal detected in the above detection processing to generate data whose signal intensity is expressed by a luminance level.

The Doppler processing unit 6 frequency-analyzes velocity information from the echo signal received from the transmission/reception unit 4 to extract a blood flow, tissue, and contrast medium echo component by the Doppler effect, and obtains blood flow information such as an average velocity, variance, and power at multiple points. The obtained blood flow information undergoes predetermined processing in the image generating circuit 7 and the like, and is displayed in color as an average velocity image, a variance image, a power image, and a combined image of them.

The image generation unit 7 generates ultrasonic images such as a B-mode image and a Cb-mode image based on the data output from the B-mode processing unit 5 and the Doppler processing unit 6. The image generation unit 7 outputs the generated ultrasonic images to the image memory 8.

The image memory 8 includes a memory which stores the ultrasonic images output for each frame from the image generating unit 7. Such an ultrasonic image can be read out as a still image or as a moving image using a plurality of frames after, for example, diagnosis.

The display control unit 9 reads out an ultrasonic image from the image memory 8 and generates the data of a diagnostic window by combining the readout image with character information or the like. The display control unit 9 causes the display 10 to display the diagnostic window based on the generated data. Note that in a mode (to be referred to as a combination mode hereinafter) of applying driving powers corresponding to a plurality of display modes such as the B mode and the Cb mode to the ultrasonic probe 2 for a predetermined time width at a time and causing the ultrasonic probe 2 to perform transmission/reception of ultrasonic waves, the display control unit 9 generates the data of a diagnostic window by laying out ultrasonic images of identical frames in the respective display modes stored in the image memory 8 on the same window and combining the resultant data with character information or the like, and causes the display 10 to display the diagnostic window based on the generated data.

The display 10 is, for example, an LCD (Liquid Crystal Display), which displays the above diagnostic window under the control of the display control unit 9.

The input device 13 includes various types of switches, buttons, a trackball, a mouse, and a keyboard which are used to input, to the apparatus body 3, various types of instructions, conditions, an instruction to set a region of interest (ROI), various types of image quality condition setting instructions, and the like from an operator.

The interface unit 14 is an interface for connecting various types of input/output devices, communication networks, external storage devices, and the like to the apparatus main body 3. It is possible to output data such as ultrasonic images, analysis results, and the like obtained by the ultrasonic diagnostic apparatus 1 to the above input/output devices, other apparatuses connected to communication networks, and the external storage devices via the interface unit 14.

The internal storage unit 12 stores data such as various kinds of scan sequences and ultrasonic transmission conditions, control programs for making the control processor 11 implement various functions, an upper limit value table 121 and parameter tables 122B and 122Cb, and the like. When the ultrasonic diagnostic apparatus 1 operates in the combination mode, an upper limit value storage area 123 is generated in the internal storage unit 12.

As described above, the acoustic powers of the ultrasonic waves transmitted from the ultrasonic probe 2 are restricted by the four types of parameters, namely Ispta.3, TI, TempRise, and MI. In a strict sense, TI is constituted by TIS, TIB, and TIC. In this embodiment, however, for the sake of simplicity, these three elements are defined as one element, i.e., TI.

In the combination mode constituted by the B mode and the Cb mode, it is necessary to control acoustic powers in the B mode and the Cb mode so as not to make the sums of values in the B mode and Cb mode exceed the upper limit values with respect to Ispta.3, TI, and TempRise (these three parameters are the first parameters in this embodiment) and not to make the maximum value of values in the B mode and the Cb mode exceed the upper limit value with respect to MI (MI is the second parameter in the embodiment).

The upper limit value table 121 describes the upper limit values of Ispta.3, TI, and TempRise. The upper limit values of Ispta.3, TI, and TempRise described in the upper limit value table 121 are distributed to the B mode and the Cb mode at, for example, predetermined ratios in accordance with transmission conditions such as a transmission waveform, transmission weighting, transmission frequency, and transmission focus. The upper limit values of Ispta.3, TI, and TempRise respectively distributed to the B mode and the Cb mode will be respectively referred to as individual upper limit values B and individual upper limit values of the respective parameters.

The upper limit value storage area 123 functions as an upper limit storage unit in this embodiment, which stores individual upper limit values B and Cb of Ispta.3, TI, and TempRise and the upper limit value MI distributed in the above manner.

The parameter table 122B is set for each of the above transmission conditions in the B mode with respect to each of the four types of parameters described above. Likewise, the parameter table 122Cb is set for each of the above transmission conditions in the Cb mode with respect to each of the four types of parameters described above.

FIG. 2 shows an example of the parameter tables 122B and 122Cb. The table shown in FIG. 2 is associated with TempRise at specific transmission conditions in the B mode or Cb mode. This table shows the relationship between TempRise and the square value of a driving voltage V applied to the ultrasonic probe 2. Note that the parameter tables 122B and 122Cb of the respective transmission conditions associated with Ispta.3 and TI also show the relationships between Ispta.3 and TI and the square values of the driving voltages V. However, the parameter tables 122B and 122Cb of the respective transmission conditions associated with MI each show the relationship between MI and the driving voltage V. For example, the relationship between each type of parameter and the driving voltage V may be experimentally measured or empirically or logically derived.

Using the parameter tables 122B and 122Cb, each having the above arrangement, will uniquely determine an acoustic power (a driving voltage in this embodiment) corresponding to a specific transmission condition and each parameter value.

The control processor 11 controls the operation of each unit of the ultrasonic diagnostic apparatus 1. In addition, the control processor 11 in this embodiment implements functions such as an acoustic power determination unit 100, an acoustic power increasing/decreasing unit 101, a parameter specifying unit 102, an acoustic power redetermination unit 103, a ratio calculation unit 104, and a warning unit 105 by executing control programs stored in the internal storage unit 12. The operation of each of the units 100 to 105 will be described later.

The adjustment knobs 15B and 15Cb are used to adjust the acoustic powers in the B mode and the Cb mode. The user operates the adjustment knobs 15B and 15Cb. Assume that in this embodiment, the user operates the adjustment knob 15B to input an instruction to decrease the acoustic power in the B mode, and operates the adjustment knob 15Cb to input an instruction to decrease the acoustic power in the Cb mode.

[Operation]

The basic operation of the ultrasonic diagnostic apparatus 1 described above will be described next with reference to FIGS. 3, 4, 5, and 6.

Figure 3:
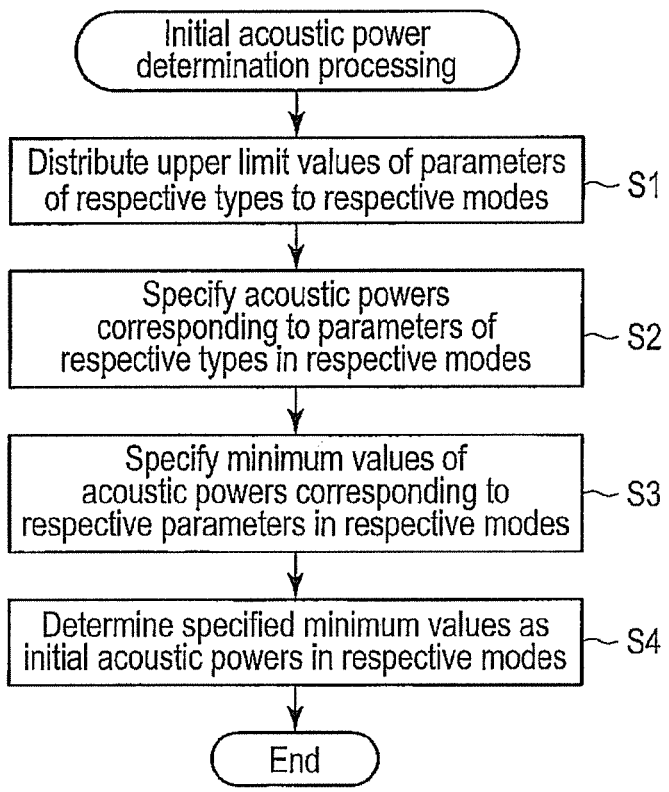
FIG. 3 is a flowchart for initial acoustic power determination processing in the first embodiment.
Figure 4:
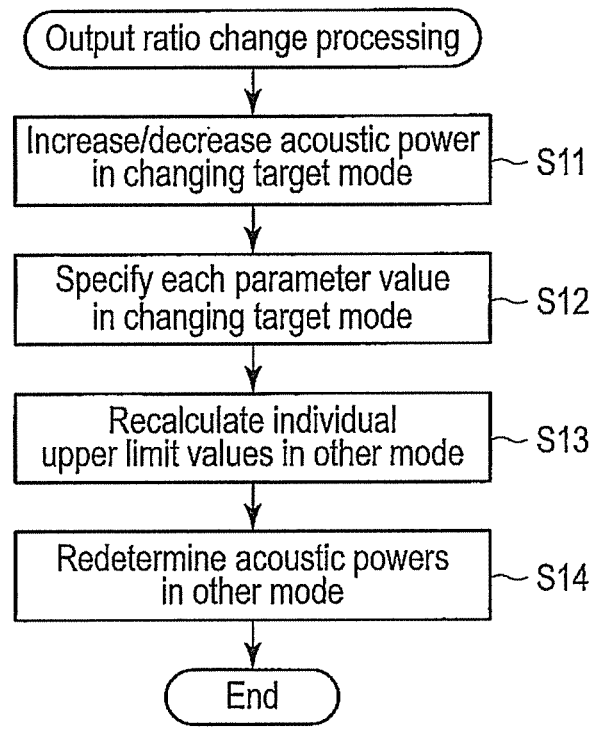
FIG. 4 is a flowchart showing output ratio change processing in the first embodiment.
Figure 5:
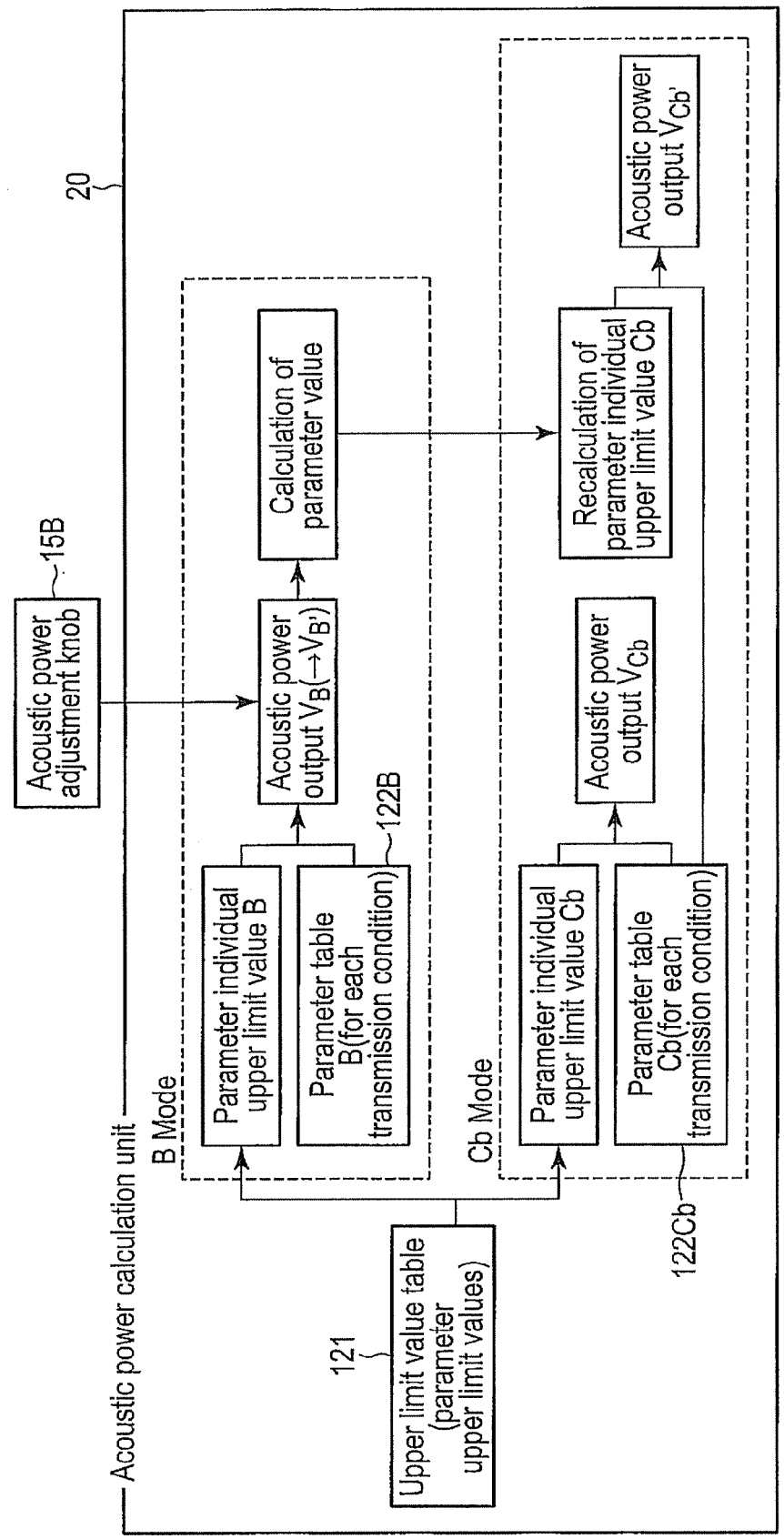
FIG. 5 is a functional block diagram of an acoustic power calculation unit in the first embodiment.

FIG. 3 is a flowchart showing operation to be performed when initial acoustic powers are determined for ultrasonic diagnosis in the combination mode. FIG. 4 is a flowchart showing operation to be performed when the acoustic powers in either of the modes are adjusted by the adjustment knobs 15B and 15Cb upon determination of initial acoustic powers. FIGS. 5 and 6 are functional block diagrams of an acoustic power calculation unit 20 constituted by the units 100 to 105 implemented by the control processor 11. FIG. 5 specifically shows a case in which the user has operated the adjustment knob 15B. FIG. 6 specifically shows a case in which the user has operated the adjustment knob 15Cb.

[Initial Acoustic Power Determination Processing]

When the user issues an instruction to start operation in the combination mode by, for example, operating the input unit 13, this apparatus starts operation in accordance with the flowchart of FIG. 3 to determine initial acoustic powers (initial driving voltages in this embodiment) in the B mode and the Cb mode.

That is, first of all, the acoustic power determination unit 100 determines the individual upper limit values B and Cb by distributing the upper limit values of Ispta.3, TI, and TempRise written in the upper limit value table 121 to the B mode and the Cb mode in accordance with transmission conditions (step S1). In this processing, for example, the acoustic power determination unit 100 distributes the upper limit values of the respective parameters written in the upper limit value table 121 in accordance with the distribution ratios of the respective parameters determined in advance for each transmission condition.

Note that as the above transmission conditions, i.e., the transmission waveform, transmission weighting, transmission frequency, and transmission focus, data stored in advance in the internal storage unit 12 or the like or data externally input via the input unit 13 or the interface unit 14 may be used.

The upper limit value storage area 123 stores the individual upper limit values B and Cb of Ispta.3, TI, and TempRise and the upper limit value of MI determined in step S1.

After step S1, the acoustic power determination unit 100 refers to the parameter tables 122B and 122Cb of the four types of parameters corresponding to transmission conditions to specify acoustic powers i.e., driving voltages, corresponding to the individual upper limit values B and Cb and the upper limit value of MI stored in the upper limit value storage area 123 for the B mode and the Cb mode (step S2). In the following description, driving voltages corresponding to the upper limit values of Ispta.3, TI, TempRise, and MI which are obtained in the B mode are respectively defined as $V_{B1}$, $V_{B2}$, $V_{B3}$, and $V_{B4}$, and driving voltages corresponding to the upper limit values of Ispta.3, TI, TempRise, and MI which are obtained in the Cb mode are respectively defined as $V_{C1}$, $V_{C2}$, $V_{C3}$, and $V_{C4}$.

Subsequently, the acoustic power determination unit 100 specifies, with respect to the B mode and the Cb mode, the minimum value of the acoustic powers specified in step S2, i.e., the minimum value of the driving voltages $V_{B1}$ to $V_{B4}$, and the minimum value of the driving voltages $V_{C1}$ to $V_{C4}$ (step S3). The acoustic power determination unit 100 determines the specified minimum value of the driving voltages $V_{B1}$ to $V_{B4}$ as an initial driving voltage $V_B$ in the B mode, and determines the minimum value of the driving voltages $V_{C1}$ to $V_{C4}$ as an initial driving voltage $V_{Cb}$ in the Cb mode (step S4).

Upon determining the initial driving voltages $V_B$ and $V_{Cb}$, the control processor 11 applies the initial driving voltages $V_B$ and $V_{Cb}$ to the ultrasonic probe 2 for a predetermined time width at a time to transmit/receive ultrasonic waves corresponding to transmission conditions. At this time, the B-mode processing unit 5 processes the echo signal obtained by the ultrasonic probe 2 at the time of application of the initial driving voltage $V_B$, and the Doppler processing unit 6 processes the echo signal obtained by the ultrasonic probe 2 at the time of application of the initial driving voltage $V_{Cb}$. The image generation unit 7 then generates B-mode and Cb-mode ultrasonic images. The image memory 8 stores the generated ultrasonic images in the respective modes. The display control unit 9 reads out each ultrasonic image and combines it with character information or the like and displays the resultant information on the display 10.

[Acoustic Power Output Ratio Change Processing]

When the user operates the adjustment knob 15B or 15Cb after the determination of the initial driving voltages $V_B$ and $V_{Cb}$, the apparatus decreases the driving voltage in the mode corresponding to the operated adjustment knob from the initial driving voltage and increases the driving voltage in the other mode, thus changing the acoustic power output ratio in each mode.

Processing associated with the above change in output ratio will be described below with reference to the flowchart of FIG. 4.

In this processing, first of all, the acoustic power increasing/decreasing unit 101 decreases the driving voltage in the changing target mode by the amount designated by the adjustment knob 15B or 15Cb (step S11). The above changing target mode is the B mode if the user has operated the adjustment knob 15B, and is the Cb mode if the user has operated the adjustment knob 15Cb.

The parameter specifying unit 102 then refers to parameter tables 122 associated with Ispta.3, TI, TempRise, and MI corresponding to the current transmission conditions, and specifies the values of Ispta.3, TI, and TempRise corresponding to the driving voltages after they have been decreased in step S11 (step S12).

The acoustic power redetermination unit 103 sequentially recalculates individual upper limit values in the mode other than the changing target mode (step S13). More specifically, the acoustic power redetermination unit 103 distributes, to the individual upper limit values in the other mode stored in the upper limit value storage area 123, the differences obtained by subtracting the values of Ispta.3, TI, and TempRise specified in step S12 from the individual upper limit values in the changing target mode stored in the upper limit value storage area 123, thereby recalculating individual upper limit values in the other mode.

The acoustic power redetermination unit 103 redetermines acoustic powers, i.e., driving voltages, in the other mode by using the recalculated individual upper limit values and the upper limit value of MI stored in the upper limit value storage area 123 (step S14). The apparatus basically performs this processing in the same procedure as that in steps S2 to S4. That is, the acoustic power redetermination unit 103 specifies driving voltages corresponding to the individual upper limit values after recalculation and the upper limit value of MI stored in the upper limit value storage area 123 by referring to the parameter table 122 in the other mode corresponding to transmission conditions, and determines the minimum value as a new driving voltage in the other mode. With step S14, the apparatus terminates the series of processing.

After the processing based on this procedure, the apparatus drives the ultrasonic probe 2 at the driving voltage set after the voltage decreasing operation in step S11 in the changing target mode. The apparatus also drives the ultrasonic probe 2 at the driving voltages redetermined in step S14 in the mode other than the changing target mode.

There will be described a concrete example of the processing associated with redetermination of output ratios in a case in which the user has operated the adjustment knob 15B to issue an instruction to decrease the initial driving voltage $V_B$.

In this case, in step S11, the apparatus decreases the initial driving voltage $V_B$ by the amount designated by the above operation. The driving voltage in the B mode after the voltage decreasing operation will be defined as an initial driving voltage $V_{B'}$ hereinafter. Subsequently, the apparatus refers to the parameter tables 122B of Ispta.3, TI, TempRise, and MI corresponding to the transmission conditions in step S12, and specifies four types of parameter values corresponding to the driving voltage $V_{B'}$.

In step S13, the apparatus recalculates the individual upper limit values Cb in the Cb mode by adding the differences between the values of Ispta.3, TI, and TempRise and the individual upper limit values B stored in the upper limit value storage area 123 to the individual upper limit values Cb in the Cb mode stored in the upper limit value storage area 123.

Figure 7:
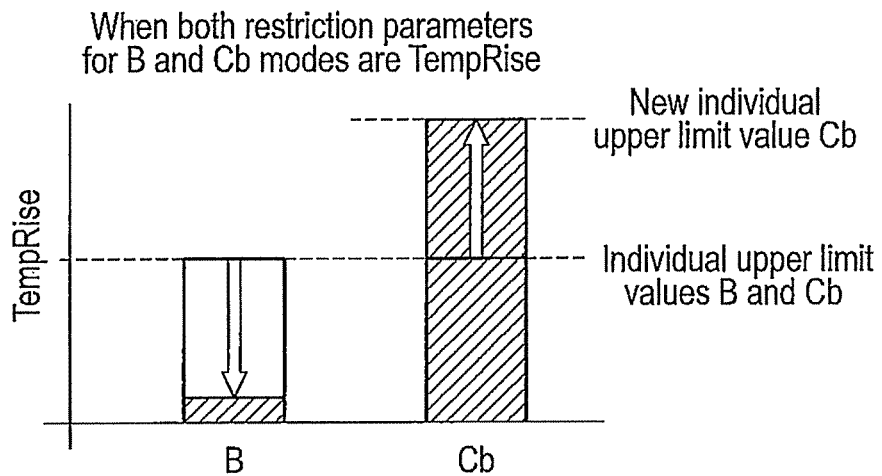
FIG. 7 is a view for explaining a concrete example in the first embodiment.

FIG. 7 shows the state of this recalculation. This is a vertical bar graph showing how the upper limit value of TempRise in each mode changes by the above recalculation when the upper limit value of TempRise is equally distributed to the B mode and the Cb mode and either parameter (to be referred to as a restriction parameter hereinafter) which is the above minimum value used to determine the initial driving voltages $V_B$ and $V_{Cb}$ is TempRise. Both values of TempRise in the respective modes before the operation of the adjustment knob 15B coincide with "individual upper limit values B and Cb" in FIG. 7. After the operation of the adjustment knob 15B, however, as the initial driving voltage $V_B$ decreases, TempRise in the B mode decreases as indicated by the downward arrow. This decrease indicated by this downward arrow is added to the individual upper limit value Cb in the Cb mode. Likewise, with regard to Ispta.3 and TI as well, the differences between the values of these parameters in the B mode and the individual upper limit values B of Ispta.3 and TI are added to the individual upper limit values Cb of Ispta.3 and TI in the Cb mode.

In step S14, the apparatus redetermines an initial driving voltage $V_{Cb'}$ by using the individual upper limit values Cb of TempRise, Ispta.3, and TI and the upper limit value of MI which have increased in the above manner.

Figure 8:
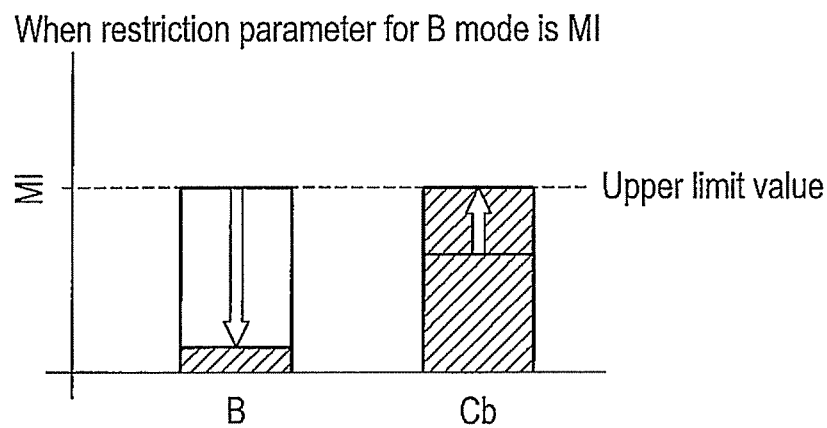
FIG. 8 is a view showing an example of a change in MI in the first embodiment.

Note that since MI is evaluated by the maximum value of the values in each mode instead of the sum of the values as described above, the upper limit value is not redistributed in step S13. FIG. 8 shows an example of how MI changes as the user decreases the acoustic power output ratio in the B mode by operating the adjustment knob 15B. This is a vertical bar graph showing how the user decreases the driving voltage in the B mode and increases the driving voltage in the Cb mode by operating the adjustment knob 15B when the restriction parameter for the initial driving voltage $V_B$ is MI. As the user decreases the driving voltage in the B mode by operating the adjustment knob 15B, MI in the B mode decreases as indicated by the downward arrow. However, since the upper limit values of MI in the B mode and the Cb mode coincide with each other, the upper limit value of MI in the Cb mode does not vary before and after the operation of the adjustment knob 15B unlike as shown in FIG. 7.

[Display of Output Ratios]

The ultrasonic diagnostic apparatus 1 in this embodiment has a function of notifying the acoustic power output ratios and the like in the B mode and the Cb mode which have been changed in the above manner. This function will be specifically described.

Figure 9:
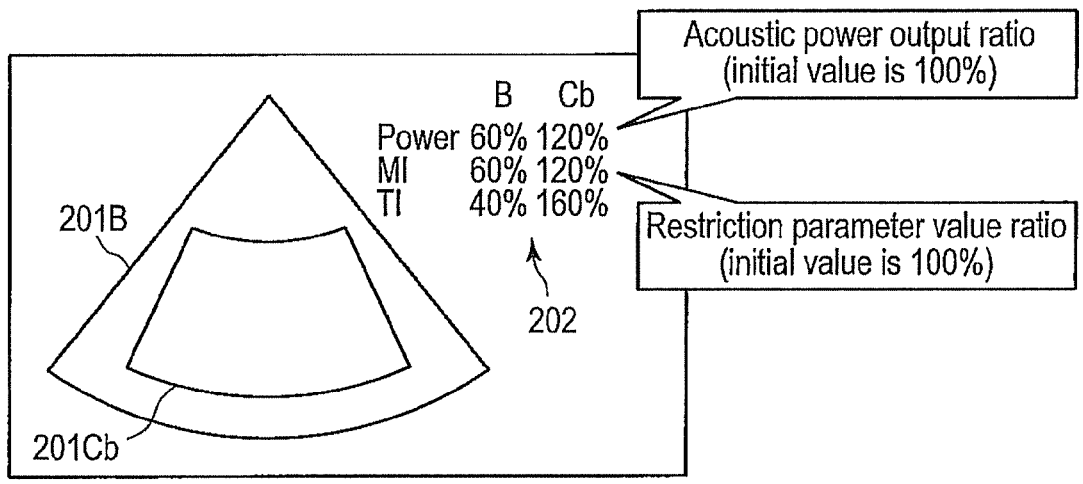
FIG. 9 is a schematic view showing an example of a diagnostic window in the first embodiment.

FIG. 9 is a schematic view showing an example of a diagnostic window 200 displayed on the display 10. The display 10 functions as a ratio notifying unit in this embodiment. The diagnostic window 200 includes a B-mode ultrasonic image 201B, a Cb-mode ultrasonic image 201Cb, and a ratio display 202. The ultrasonic images 201B and 201C in the respective modes are updated in real time while the ultrasonic probe 2 is driven in the combination mode.

The ratio display 202 describes, for example, the acoustic powers (Power) in the B mode and the Cb mode and the values of MI and TI in percentage with reference to the values set before adjustment by the adjustment knobs 15B and 15Cb. The ratio calculation unit 104 calculates these ratios every time the user operates the adjustment knobs 15B and 15Cb. The acoustic power ratios in the respective modes are obtained by dividing the current driving voltages $V_{B'}$ and $V_{Cb'}$ by the initial driving voltages $V_B$ and $V_{Cb}$. The ratios of MI are obtained by dividing the current values of MI in the respective modes by the upper limit values of MI defined in the upper limit value table 121. The ratios of TI are obtained by dividing the current values of TI in the respective modes by the individual upper limit values B and Cb of TI stored in the upper limit value storage area 123. The parameter specifying unit 102 may specify the current values of MI and TI in the respective modes used in this case by using the current driving voltages $V_{B'}$ and $V_{Cb'}$ and the parameter tables 122B and 122Cb.

Although FIG. 9 shows only the acoustic power ratios and MI and TI ratios, Ispta.3 and TempRise ratios may be shown. Furthermore, the ratios of TIS, TIB, and TIC constituting TI may be shown.

In addition, this graph may also describe the upper limits of acoustic power and parameters of the respective types, which can be changed by the operation of the adjustment knobs 15B and 15Cb, in percentage, with the initial driving voltages $V_B$ and $V_{Cb}$ and the values of parameters in the respective modes corresponding to them being in the state of "0%". In this case, it is possible to obtain the upper limits of Ispta.3, TI, and TempRise in the respective modes by dividing the maximum values of the individual upper limit values B and Cb, i.e., the upper limit values of these parameters defined in the upper limit value table 121, by the values of the parameters corresponding to the initial driving voltages $V_B$ and $V_{Cb}$. In addition, the upper limits of MI in the respective modes are obtained by, for example, dividing the upper limit values of MI defined in the upper limit value table 121 by the values of MI in the respective modes which correspond to the initial driving voltages $V_B$ and $V_{Cb}$. Furthermore, the upper limits of acoustic powers in the respective modes are obtained by, for example, dividing the driving voltages in the respective modes, determined by performing the processing in steps S2 to S4 using the maximum values of the individual upper limit values B and Cb in the respective modes, i.e., the upper limit values defined in the upper limit value table 121, by the initial driving voltage $V_B$ and $V_{Cb}$ in the respective modes.

[Warning Processing to be Performed when Restriction Parameter is MI]

As described with reference to FIG. 8, since MI is evaluated by the maximum value in each mode, the upper limit value is not distributed to each mode and is constant in each mode. For this reason, if a restriction parameter for one mode is MI, it is not possible to increase the acoustic power in the one mode even by decreasing the acoustic power in the other mode and redistributing the upper limit values of Ispta.3, TI, and TempRise. That is, executing the processing in steps S11 to S14 will only decrease the acoustic power in a changing target mode but will not change the acoustic power in a mode other than the changing target mode.

In consideration of this, in this embodiment, if a restriction parameter for at least one of the initial driving voltages $V_B$ and $V_{Cb}$ determined through initial acoustic power determination processing is MI, the warning unit 105 warns the user about this.

The apparatus performs this warning by, for example, displaying a predetermined warning message on the diagnostic window 200 shown in FIG. 9. Alternatively, the apparatus may perform warning by outputting a status indicating that one restriction parameter is MI to a device communicatively connected to the ultrasonic diagnostic apparatus 1 via the interface unit 14 or by outputting speech from a loudspeaker (not shown).

[Display Processing of Past Image]

If the user operates the adjustment knobs 15B and 15Cb to decrease the acoustic power in either of the B mode and the Cb mode to 0, he/she cannot obtain any ultrasonic image in the corresponding mode.

In consideration of this, in this embodiment, when the acoustic power, i.e., the driving voltage, in either of the B mode and the Cb mode becomes 0, the apparatus displays an image in the corresponding mode which was generated in the past on a diagnostic window.

Figure 10:
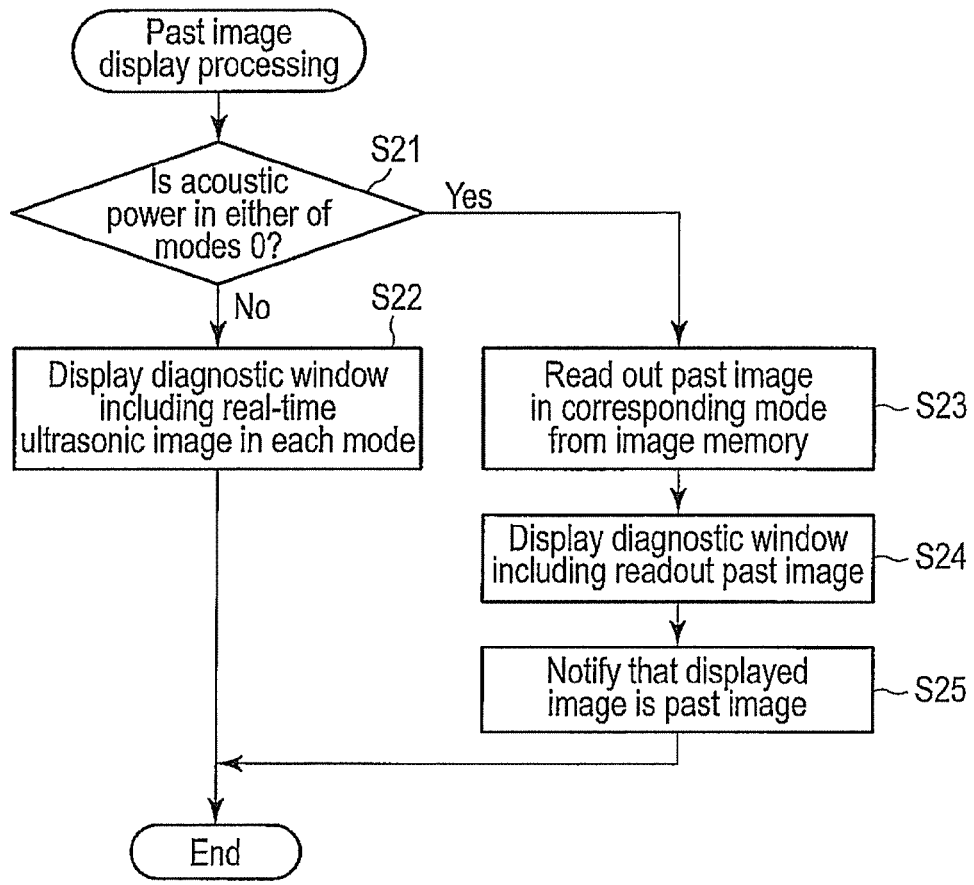
FIG. 10 is a flowchart for past image display processing in the first embodiment.

For example, the display control unit 9 implements this processing by performing operation in accordance with the flowchart shown in FIG. 10. That is, immediately after the execution of the processing in steps S11 to S14, the display control unit 9 determines whether the driving voltages $V_{B'}$ and $V_{Cb'}$ in the B mode and the Cb mode are 0 (step S21). If neither of the driving voltages $V_{B'}$ and $V_{Cb'}$ is 0 (NO in step S21), the display control unit 9 sequentially generates the data of a diagnostic window by using B-mode and Cb-mode ultrasonic images which are generated by the image generation unit 7 based on the data output from the B-mode processing unit 5 and Doppler processing unit 6 and stored in the image memory 8, and outputs the generated data to the display 10 (step S22). As a result, the display 10 displays a diagnostic window including B-mode and Cb-mode real-time ultrasonic images.

On the other hand, if either of the driving voltages $V_{B'}$ and $V_{Cb'}$ is 0 (YES in step S21), the display control unit 9 reads out, from the image memory 8, an image in the mode in which the driving voltage is 0, which was generated in the past and captured when the driving voltage in the mode was not 0 (step S23). The image to be read out may be the one captured before a predetermined period of time (for example, about several sec) or the one captured immediately before the operation of an adjustment knob 15 which served as a trigger for the start of the processing in steps S11 to S14.

After step S23, the display control unit 9 generates the data of a diagnostic window by using the readout image and the ultrasonic image in the mode in which the driving voltage is not 0, which is sequentially stored in the image memory 8, and outputs the generated data to the display 10 (step S24). As a result, the apparatus changes the ultrasonic image in the mode in which the driving voltage is 0, which is displayed on the display 10, from the real-time image to a past image which is a still image.

After step S24, the display control unit 9 notifies the user of information indicating that an ultrasonic image in the mode in which the driving voltage is 0 is a past image (step S25). The display control unit 9 performs this notification by, for example, displaying a predetermined message on a diagnostic window. Alternatively, the ultrasonic diagnostic apparatus 1 may output a status indicating that an ultrasonic image in the mode in which the driving voltage is 0 is a past image to a device communicatively connected to the ultrasonic diagnostic apparatus 1 via the interface unit 14 or may notify the user of the corresponding information by outputting speech from a loudspeaker (not shown).

Although this embodiment has exemplified the case in which when either of the driving voltages $V_{B'}$ and $V_{Cb'}$ is 0, a past image is displayed, the apparatus may display a past image when either of the driving voltages $V_{B'}$ and $V_{Cb'}$ becomes less than a predetermined threshold.

As described above, when the user operates the adjustment knob 15B or 15Cb to input an instruction to decrease the acoustic power in the B mode or the Cb mode, the ultrasonic diagnostic apparatus 1 according to this embodiment decreases the acoustic power in the changing target mode in accordance with the instruction. In addition, the apparatus increases the acoustic power in the other mode by distributing a margin corresponding to the individual upper limit value of each parameter in the changing target mode which has been generated due to this decrease to the individual upper limit value in the other mode. With this arrangement, the user can easily improve the sensitivity of a desired mode while observing a restriction by each parameter, by only operating the adjustment knobs 15B and 15Cb.

The ultrasonic diagnostic apparatus 1 also displays, on a diagnostic window, the ratios of acoustic powers and values of MI, TI, and the like in the B mode and the Cb mode before and after adjustment with the adjustment knobs 15B and 15Cb. Displaying such ratios allows the user to easily comprehend the adjustment states and the like of the acoustic powers in the B mode and the Cb mode.

In addition, when the acoustic power, i.e., the driving voltage in either of the modes becomes 0 or less than the threshold upon operation of either of the adjustment knobs 15B and 15Cb, the ultrasonic diagnostic apparatus 1 changes the ultrasonic image in the corresponding mode which is displayed on a diagnostic window into an ultrasonic image in the corresponding mode which was captured in the past. Even when the driving voltage in either of the modes becomes 0 or less than the above threshold, therefore, displaying a past image in this manner will prevent a situation in which no ultrasonic image in the mode is displayed or an ultrasonic image which is too poor to be used for diagnosis is displayed.

When a restriction parameter for the initial acoustic power, i.e., the initial driving voltage in either of the modes is MI, the ultrasonic diagnostic apparatus 1 also warns that the acoustic power in the other mode cannot be changed. This allows the user to easily comprehend the mode in which the acoustic power cannot be changed.

In addition to these effects, the arrangement of this embodiment allows to obtain various kinds of preferable effects.

Second Embodiment

The second embodiment will be described next.

If a restriction parameter for either of the B mode and the Cb mode is MI when determining initial acoustic powers, an ultrasonic diagnostic apparatus 1 according to this embodiment redistributes margins of the individual upper limit values of Ispta.3, TI, and TempRise which are distributed to the corresponding mode to the other mode to redetermine an initial acoustic power in the corresponding mode. This embodiment differs in this regard from the first embodiment.

Since the arrangement of the ultrasonic diagnostic apparatus 1, output ratio change processing, and the like are the same as those in the first embodiment, the same reference numerals as in the first embodiment denote the same parts in the second embodiment, and a description of them will be omitted.

In initial acoustic power determination processing in this embodiment, the respective units of the ultrasonic diagnostic apparatus 1 operate in accordance with the flowchart of FIG. 11.

First of all, as in the first embodiment, an acoustic power determination unit 100 determines individual upper limit values B and Cb by distributing the upper limit values of Ispta.3, TI, and TempRise written in an upper limit value table 121 to the B mode and the Cb mode in accordance with transmission conditions (step S1). The upper limit value storage area 123 stores the determined individual upper limit values B and Cb of Ispta.3, TI, and TempRise and the upper limit values of MI.

The acoustic power determination unit 100 then refers to parameter tables 122B and 122Cb of four types of parameters corresponding to transmission conditions, and specifies acoustic powers, i.e., driving voltages, corresponding to the individual upper limit values B and Cb and the upper limit values of MI in the B mode and the Cb mode (step S2). After step S2, the acoustic power determination unit 100 specifies the minimum value of driving voltages $V_{B1}$ to $V_{B4}$ and the minimum value of driving voltages $V_{C1}$ to $V_{C4}$ specified in step S2 (step S3). After step S3, the acoustic power determination unit 100 determines the minimum value of the specified driving voltages $V_{B1}$ to $V_{B4}$ as an initial driving voltage $V_B$ in the B mode, and determines the minimum value of the driving voltages $V_{C1}$ to $V_{C4}$ as an initial driving voltage $V_{Cb}$ in the Cb mode (step S4).

After steps S1 to S4, the acoustic power determination unit 100 determines whether a restriction parameter for either of the modes is MI, and more specifically whether the minimum value specified in step S3 in either of the modes is MI (step S5).

If the restriction parameter for either of the B mode and the Cb mode is not MI or the restriction parameters for the two modes are MI (NO in step S5), the acoustic power determination unit 100 terminates the initial acoustic power determination processing. Subsequently, the apparatus drives an ultrasonic probe 2 at the initial driving voltages $V_B$ and $V_{Cb}$ determined in step S4 to perform diagnostic processing in the combination mode.

If the restriction parameter for either of the modes is MI (YES in step S5), a parameter specifying unit 102 refers to a parameter table 122 associated with Ispta.3, TI, TempRise, and MI corresponding to the current transmission conditions, and specifies the values of Ispta.3, TI, and TempRise corresponding to the initial driving voltage in the corresponding mode determined in step S4 (step S6).

Subsequently, an acoustic power redetermination unit 103 recalculates individual upper limit values in the mode for which the restriction parameter is not MI (step S7). More specifically, the acoustic power redetermination unit 103 redistributes the differences between the values of Ispta.3, TI, and TempRise specified in step S6 and the individual upper limit values in the mode, stored in an upper limit value storage area 123, for which the restriction parameter is MI to the individual upper limit values in the other mode stored in the upper limit value storage area 123, thereby recalculating individual upper limit values in the other mode.

The acoustic power redetermination unit 103 then redetermines an initial driving voltage in the other mode by using the recalculated individual upper limit values and upper limit value of MI (step S8). This processing is basically performed in the same procedure as that in steps S2 to S4. That is, the acoustic power redetermination unit 103 specifies driving voltages corresponding to the individual upper limit values and the upper limit value of MI after the above recalculation by referring to the parameter table 122 for the other mode corresponding to the transmission conditions, and determines the minimum value as a new initial driving voltage in the other mode. With step S8, the apparatus terminates the series of processing.

Upon completion of the initial acoustic power determination processing through steps S6 to S8, the apparatus drives the ultrasonic probe 2 at the initial driving voltage determined in step S4 in the mode for which the restriction parameter is MI, and at the initial driving voltage redetermined in step S8 in the other mode, thereby performing diagnostic processing in the combination mode.

A concrete example of initial acoustic power determination processing based on the above procedure will be described with reference to FIGS. 12 and 13.

Figure 12:
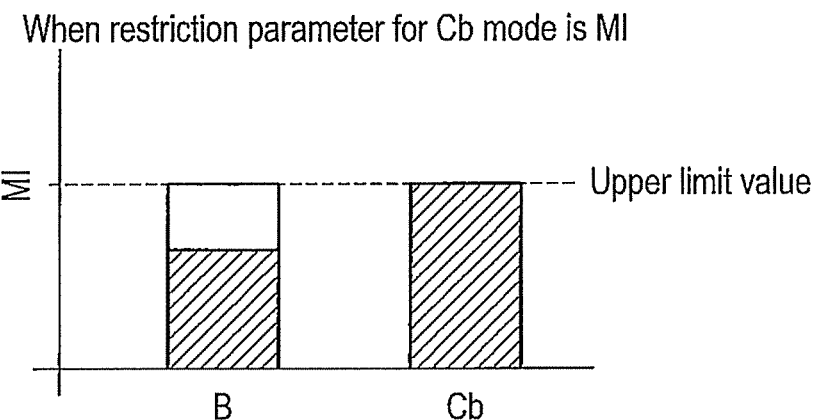
FIG. 12 is a view for explaining a concrete example in the second embodiment.

In this concrete example, as shown in FIG. 12, the restriction parameter for the initial driving voltage $V_B$ is not MI, and the restriction parameter for the initial driving voltage $V_{Cb}$ is MI. When performing the processing in step S7 in this state, the apparatus redistributes the margins of the individual upper limit values Cb of Ispta.3, TI, and TempRise in the Cb mode to the individual upper limit values B of Ispta.3, TI, and TempRise in the B mode.

Figure 13:
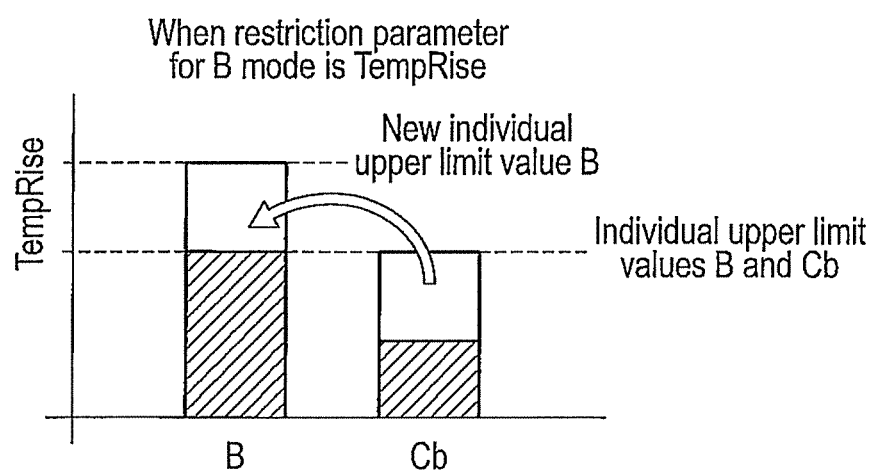
FIG. 13 is a view for explaining a concrete example in the second embodiment.

In this case, if, for example, the restriction parameter for the initial driving voltage $V_B$ determined in step S4 is TempRise as shown in FIG. 13, an individual upper limit value B increases by the portion distributed in the processing in step S7, thus generating a margin of TempRise. As a result, the initial driving voltage $V_B$ determined in the processing in step S8 is higher than at least the value determined in step S4.

As described above, when determining an initial acoustic power, i.e., an initial driving voltage, in each mode, if the restriction parameter for either of the modes is MI, the ultrasonic diagnostic apparatus 1 according to this embodiment automatically distributes the margins of the individual upper limit values of Ispta.3, TI, and TempRise in the mode to the other mode, and redetermines an initial driving voltage in the other mode. This arrangement maximizes the acoustic powers in the respective modes at the time of determination of initial acoustic powers within a range in which the acoustic powers in the respective modes do not exceed the upper limit values of the respective parameters, thereby obtaining better diagnostic images in the respective modes.

Obviously, this embodiment can obtain the same effects as those described in the first embodiment.

(Modification)

The arrangements disclosed in the respective embodiments can be variously modified and embodied at the execution stage. The following are concrete modifications.

(1) Each embodiment described above has exemplified the case in which the apparatus adjusts the acoustic power in each mode of the combination mode constituted by the B mode and the Cb mode. However, it is possible to apply the arrangement disclose in each embodiment described above to the adjustment of acoustic power in each mode of the combination mode constituted by the B mode and the D mode and of the combination mode constituted by the B mode, the Cb mode, and the D mode.

In addition, it is possible to apply the arrangement disclosed in each embodiment described above to the adjustment of an acoustic power in each mode of the combination mode including a mode accompanied by the administration of a contrast medium (microbubble contrast medium or the like) into an object. For example, modes accompanied by the administration of a contrast medium include the CHI (Contrast Harmonic Imaging) mode of displaying an image based on high-frequency components generated due to the nonlinear effect produced in ultrasonic waves entering a contrast medium and the MFI (Micro Flow Imaging) mode of visualizing how re-perfusion occurs upon destruction of a contrast medium with strong ultrasonic waves.

In the combination mode constituted by three or more modes, if it is necessary to determine an acoustic power in each mode, an adjustment knob for acoustic power may be provided for each mode. In output ratio change processing executed upon operation of either of the adjustment knobs, the apparatus may distribute the margins of individual upper limit values in a changing target mode to the individual upper limit values in all the modes except for the changing target mode at predetermined distribution ratios in step S13, and redetermine acoustic powers in all the other modes by using the individual upper limit values after the distribution in step S14. In addition, in the initial acoustic power determination processing described in the second embodiment, the apparatus may distribute the margins of individual upper limit values in a mode for which the restriction parameter is MI to the individual upper limit values in all the modes other than the mode for which the restriction parameter is MI at predetermined distribution ratios in step S7, and redetermine acoustic powers in all the other modes by using the individual upper limit values after the distribution in step S8.

(2) Each embodiment described above has exemplified the case in which the user decreases the driving voltage in the B mode from the initial driving voltage $V_B$ with the adjustment knob 15B, and decreases the driving voltage in the Cb mode from the initial driving voltage $V_{Cb}$ with the adjustment knob 15Cb. However, the user may increase the driving voltage in the B mode from the initial driving voltage $V_B$ with the adjustment knob 15B, and increase the driving voltage in the Cb mode from the initial driving voltage $V_{Cb}$ with the adjustment knob 15Cb. When the user increases the driving voltage in a changing target mode in this manner, either of the parameters may exceed the individual upper limit value in the corresponding mode which is stored in the upper limit value storage area 123. In this case, the difference associated with this parameter calculated in step S13 becomes a negative number, and the difference as this negative number is distributed to the individual upper limit value in the other mode. As a consequence, the individual upper limit value in the other mode decreases.

This will basically decrease the driving voltage in the other mode which is calculated in step S14.

(3) Each embodiment described above has exemplified the case in which the acoustic power in each mode is controlled by increasing/decreasing a driving voltage. However, it is possible to control acoustic power by other methods, for example, increasing/decreasing the current to be supplied to the ultrasonic probe 2.

(4) In each embodiment described above, the control processor 11 implements the respective functions including the acoustic power determination unit 100, the acoustic power increasing/decreasing unit 101, the parameter specifying unit 102, the acoustic power redetermination unit 103, the ratio calculation unit 104, and the warning unit 105 by executing control programs stored in the internal storage unit 12. However, each embodiment is not limited to this, and may download the above control programs from a predetermined network into the ultrasonic diagnostic apparatus 1 or install, in the ultrasonic diagnostic apparatus 1, programs for implementing the same functions stored in a recording medium. As a recording medium, a CD-ROM, USB memory, or the like can be used. In addition, it is possible to use a recording medium in any form as long as a device built in or connected to the ultrasonic diagnostic apparatus 1 can read the medium. In addition, the functions obtained by installing or downloading such programs in advance may be implemented in cooperation with the OS (Operating System) or the like in the ultrasonic diagnostic apparatus 1.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe configured to transmit and receive ultrasonic waves having acoustic powers based on supplied powers, the acoustic powers corresponding to a plurality of display modes for a predetermined time width at a time;
transmission circuitry configured to supply powers to the ultrasonic probe;
an upper limit storage memory configured to store upper limit values of parameters for restricting the acoustic powers in the respective display modes, wherein the parameters include an index associated with an action of ultrasonic waves on a living body, the first parameter including at least one of Ispta (spatial-peak temporal average Intensity), TI (Thermal Index), and an increase in surface temperature of the ultrasonic probe, and the second parameter comprises MI (Mechanical Index); and
processing circuitry configured to
determine the acoustic powers in the respective display modes so as not to exceed upper limit values of the parameters stored in the upper limit storage memory;
input an instruction to increase/decrease an acoustic power, of the acoustic powers determined by the processing circuitry, which is associated with a specific display mode;
specify the parameter value in the specific display mode in accordance with an input from the processing circuitry;
determine an upper limit value of the parameter in a display mode different from the specific display mode based on the upper limit value of the parameter in the specific display mode stored in the upper limit storage memory and the parameter value specified by the processing circuitry; and
control the transmission circuitry to supply a power to the ultrasonic probe in accordance with the specified parameter value in the specific display mode, and supply a power to the ultrasonic probe in accordance with the determined upper limit in in the display mode different from the specific display mode.

2. The ultrasonic diagnostic apparatus of claim 1, wherein the processing circuitry distributes a difference between the upper limit value of the parameter in the specific display mode stored in the upper limit storage memory and the parameter value specified by the processing circuitry to the upper limit value of the parameter in the different display mode stored in the upper limit storage memory, and redetermines an acoustic power in the different display mode so as not to exceed an upper limit value after the distribution.

3. The ultrasonic diagnostic apparatus of claim 2, further comprising:
a ratio calculation circuit configured to calculate ratios between acoustic powers in the respective display modes which are determined by the acoustic power determination circuit and acoustic powers in the respective display modes after being changed accompanying input of the instruction to increase/decrease from the increase/decrease instruction circuit; and
a ratio notifying circuit configured to notify the ratios calculated by the comparison calculation circuit.

4. The ultrasonic diagnostic apparatus of claim 1, further comprising a display control circuit configured to, when all acoustic powers in the respective display modes are 0 or not less than a predetermined threshold, make a predetermined display circuit display ultrasonic images in the respective display modes in real time which are obtained by driving the ultrasonic probe with the respective acoustic powers, and to, when any of the acoustic powers in the respective display modes becomes 0 or less than the threshold upon input of an instruction to increase/decrease from the processing circuitry, change an ultrasonic image in the corresponding display mode to be displayed on the display circuit to an ultrasonic image in the corresponding display mode which was obtained in the past.

5. The ultrasonic diagnostic apparatus of claim 2, wherein the upper limit storage memory stores upper limit values of a first parameter evaluated by a sum of values in the respective display modes which are distributed to the respective display modes, and upper limit values of a second parameter evaluated by a maximum value of values in the respective display modes, wherein the first parameter includes an index associated with an action of ultrasonic waves on a living body, wherein the second parameter is different from the first parameter,
the processing circuitry determines the acoustic powers in the respective display modes so as not to exceed the upper limit value of the first parameter and the upper limit value of the second parameter in the display modes stored in the upper limit storage memory,
the processing circuitry specifies the first parameter value in the specific display mode based on an acoustic power having undergone an increase/decrease in accordance with input from the processing circuitry, and the processing circuitry distributes a difference between the upper limit value of the first parameter in the specific display mode stored in the upper limit storage memory and the first parameter value specified by the processing circuitry to the upper limit value of the first parameter in the different display mode stored in the upper limit storage memory, and redetermines an acoustic power in the different display mode so as not to exceed an upper limit value after the distribution and the upper limit value of the second parameter stored in the upper limit storage memory.

6. The ultrasonic diagnostic apparatus of claim 5, further comprising a table provided for each of the first parameter and the second parameter and configured to define acoustic powers corresponding to parameter values of the first parameter and the second parameter, wherein the processing circuitry specifies acoustic powers, in the respective display modes, which correspond to the upper limit values of the first parameter and second parameter in the respective display modes stored in the upper limit storage memory by using the table, and determines a minimum value of the respective specified acoustic powers as an acoustic power in the display mode, and the processing circuitry specifies acoustic powers respectively corresponding to the upper limit value of the first parameter after the distribution and the upper limit value of the second parameter stored in the upper limit storage memory by using the table, and redetermines a minimum value of the respective specified acoustic powers as an acoustic power in the different display mode.

7. The ultrasonic diagnostic apparatus of claim 6, further comprising a warning circuit configured to, when an acoustic power corresponding to the upper limit value of the second parameter in either of the display modes is the minimum value, warn that an acoustic power in the corresponding display mode is not configured to be changed.

8. The ultrasonic diagnostic apparatus of claim 6, wherein when the acoustic power corresponding to the upper limit value of the second parameter in either of the display modes is the minimum value, the processing circuitry specifies the first parameter value in the corresponding display mode based on the acoustic power, and the processing circuitry distributes a difference between the upper limit value of the first parameter in the corresponding display mode stored in the upper limit storage memory and the first parameter value specified by the processing circuitry to the upper limit value of the first parameter in a display mode different from the corresponding display mode stored in the upper limit storage memory, and redetermines an acoustic power in the different display mode so as not to exceed an upper limit value after the distribution and the upper limit value of the second parameter stored in the upper limit storage memory.

9. An ultrasonic diagnostic apparatus comprising:

an ultrasonic probe configured to transmit and receive ultrasonic waves having acoustic powers based on supplied powers, the acoustic powers corresponding to a plurality of display modes for a predetermined time width at a time;

transmission circuitry configured to supply powers to the ultrasonic probe;

an upper limit storage memory configured to store upper limit values of a first parameter evaluated by a sum of values in the respective display modes which are distributed to the respective display modes, and upper limit values of a second parameter evaluated by a maximum value of values in the respective display modes, wherein the first parameter includes an index associated with an action of ultrasonic waves on a living body, the first parameter including at least one of Ispta (spatial-peak temporal average Intensity), TI (Thermal Index), and an increase in surface temperature of the ultrasonic probe, and the second parameter comprises MI (Mechanical Index), wherein the second parameter is different from the first parameter;

a table configured to define acoustic powers corresponding to the parameter values for each of the first parameter and the second parameter; and processing circuitry configured to specify, for the respective display modes, acoustic powers corresponding to the upper limit values of the first parameter and second parameter in the display modes stored in the upper limit storage memory by using the table, and to determine a minimum value of the specified respective acoustic powers as an acoustic power in the display mode;

when the acoustic power corresponding to the upper limit value of the second parameter in either of the display modes is the minimum value, specify the first parameter value in the display mode corresponding to the acoustic power by using the table;

distribute a difference between the upper limit value of the first parameter in the corresponding display mode stored in the upper limit storage memory and the first parameter value specified by the processing circuitry to the upper limit value of the first parameter in a display mode different from the corresponding display mode stored in the upper limit storage memory, and to redetermine an acoustic power in the different display mode so as not to exceed an upper limit value after the distribution and the upper limit value of the second parameter stored in the upper limit storage memory; and control the transmission circuitry to supply a power to the ultrasonic probe in accordance with the first parameter value in the corresponding display mode, and supply a power to the ultrasonic probe in accordance with the determined acoustic power in the different display mode.

10. A transmission/reception control method of driving an ultrasonic probe with acoustic powers corresponding to a plurality of display modes for a predetermined time width at a time so as to transmit and receive ultrasonic waves, comprising:

determining the acoustic powers in the respective display modes so as not to exceed upper limit values of parameters for restricting the acoustic powers in the respective display modes which are stored in a predetermined storage memory;

specifying, in response to input of an instruction to increase/decrease an acoustic power in a specific display mode of the acoustic powers determined by the determining step, the parameter value in the specific display mode;

determining an upper limit value of the parameter in a display mode different from the specific display mode based on the upper limit value of the parameter in the specific display mode stored in the storage memory and the parameter value specified by the specifying step; and controlling the transmission circuitry to supply a power to the ultrasonic probe in accordance with the specified parameter value in the specific display mode, and supply a power to the ultrasonic probe in accordance with the determined upper limit in the display mode different from the specific display mode.

11. The ultrasonic diagnostic apparatus according to claim 1, wherein the processing circuitry controls the transmission circuitry to increase/decrease a voltage or a current to be supplied to the ultrasonic probe.

12. The ultrasonic diagnostic apparatus according to claim 9, wherein the processing circuitry controls the transmission circuitry to increase/decrease a voltage or a current to be supplied to the ultrasonic probe.

* * * * *